United States Patent [19]

Band et al.

[11] Patent Number: 5,395,505
[45] Date of Patent: Mar. 7, 1995

[54] CATION-SELECTIVE POLYMERIC ELECTRODES

[75] Inventors: David M. Band, Surblton; Robert A. F. Linton, Putney, both of United Kingdom

[73] Assignee: Monitoring Technology Limited, London, United Kingdom

[21] Appl. No.: 211,926

[22] PCT Filed: Oct. 29, 1992

[86] PCT No.: PCT/GB92/01979

§ 371 Date: Apr. 28, 1994

§ 102(e) Date: Apr. 28, 1994

[87] PCT Pub. No.: WO93/09427

PCT Pub. Date: May 13, 1993

[30] Foreign Application Priority Data

Oct. 31, 1991 [GB] United Kingdom ............ 9123083

[51] Int. Cl.⁶ .............. G01N 27/26; A61B 5/02; A61B 5/04
[52] U.S. Cl. ............... 204/418; 204/435; 128/668; 128/670; 128/696; 128/700
[58] Field of Search ............ 204/418, 435; 128/668, 128/670, 696, 700

[56] References Cited

U.S. PATENT DOCUMENTS

| | | | |
|---|---|---|---|
| 4,772,033 | 9/1988 | Nash | 277/174 |
| 5,102,527 | 4/1992 | Shibata et al. | 204/418 |
| 5,112,471 | 5/1992 | Shibata et al. | 204/418 |
| 5,165,445 | 11/1992 | Vertanen | 137/493.6 |
| 5,240,027 | 8/1993 | Vertanen | 137/73 |
| 5,286,365 | 2/1994 | Shu | 204/418 |
| 5,312,537 | 5/1994 | Harrison et al. | 204/418 |

FOREIGN PATENT DOCUMENTS

| | | |
|---|---|---|
| 587512 | 4/1947 | United Kingdom . |
| 614962 | 12/1948 | United Kingdom . |
| 784204 | 10/1957 | United Kingdom . |
| 981778 | 1/1965 | United Kingdom . |
| 1151729 | 5/1969 | United Kingdom . |
| 1231760 | 5/1971 | United Kingdom . |
| 1427990 | 3/1976 | United Kingdom . |
| 2225060 | 5/1990 | United Kingdom . |

*Primary Examiner*—John Niebling
*Assistant Examiner*—Bruce F. Bell
*Attorney, Agent, or Firm*—Fish & Richardson

[57] ABSTRACT

A cation-sensitive electrode which comprises an internal reference electrode, an internal reference solution and a cation-responsive membrane, characterized in that the internal reference solution contains a saturated solution of a salt of a cation other than the cation for which the cation-responsive membrane is primarily selective, the internal reference solution being formed in situ by hydration of a combination of the salt of the cation with a hygroscopic material, bu absorption of water from the atmosphere and/or by hydration of the hygroscopic material when the electrode is put into use, thereby forming the internal reference solution.

20 Claims, 1 Drawing Sheet

CATION-SELECTIVE POLYMERIC ELECTRODES

CATION-SELECTIVE POLYMERIC ELECTRODES

The present invention relates to improvements in cation-selective electrodes and, in particular, to a method of stabilizing the internal or reference potential of a cation-selective electrode to reduce the disadvantage of a large temperature dependent voltage.

Cation-selective electrodes are generally membrane-based devices, involving cation-responsive membrane materials which are selective for the passage of particular cations through the membrane. They may be used for the measurement of active species in liquids.

Cation-selective electrodes are generally used in the potentiometric mode and the cation-responsive membrane establishes a voltage difference between the two solutions in contact with its surfaces, i.e. the test solution and the internal reference solution. The voltage difference is related to the difference in the logarithms of the concentration of the cation to which the membrane is selective in the two solutions. The cation-selective electrode is normally incorporated into an electrochemical cell with an internal standard reference electrode contacting the internal reference solution and a separate reference electrode contacting the analyte or test solution, usually via a salt bridge. In order for the voltage of the cell not to drift with time it is important that the concentration of the cations in the internal reference solution is kept stable. A convenient way of stabilizing the cation concentration in the internal reference solution is to use a saturated solution with the cations in solution to contact with crystals of their salt. This method has the advantage that variations in the water content of the electrolyte do not affect the concentration of the cation. This method has the disadvantage that if the electrode is used for measuring low concentrations of the cation, a large voltage is generated across the cation-selective membrane. Furthermore, voltage is dependent upon the temperature of the cell and the temperature coefficient that results is inconvenient for many applications. The temperature compensation of the measurements made with cation-sensitive electrodes is becoming of increasing importance as more measurements are made outside the laboratory e.g. in environmental work and in potential biochemical applications.

All of the ligands or ionophores which are used to make cation-selective electrodes show varying degrees of cross-sensitivity with cations other than the particular cation to which they are primarily sensitive. This is normally a disadvantage. We have now used this particular property in devising a method of stabilizing the internal or reference potential of a cation-sensitive electrode reducing the disadvantage of the large temperature dependent voltage.

SUMMARY OF THE INVENTION

Accordingly, the present invention provides a cation-sensitive electrode which comprises an internal reference electrode, an internal reference solution and a cation-responsive membrane, characterized in that the internal reference solution contains a saturated solution of a salt of a cation other than the cation for which the cation-responsive membrane is primarily selective, the internal reference solution being formed in situ by hydration of a combination of a hygroscopic material with the salt of the cation other than the cation for which the cation-responsive membrane is primarily selective, either by absorption of water from the atmosphere and/or by hydration of the hygroscopic material when the electrode is put into use, thereby forming the internal reference solution.

In the present invention the cross sensitivity of the cation-responsive membranes is used to allow the internal reference solutions to comprise saturated solutions of cations which are normally considered to be interferents. The high concentration of the interfering cation is constant in the saturated solution which comprises the internal reference solution, but is only equivalent to a low concentration of the cation for which the cation-responsive membrane is selective. The membrane potential is reduced by the ratio of the selectivity of the membrane to the cation for which the membrane is selective and the interfering cation. This results in a lower offset potential and with it a reduction in the temperature coefficient of the sensor. The cation-sensitive electrode also has a stable performance and does not exhibit significant potential drift.

Specific examples of cation-responsive membranes/interfering ions which may be used in the present invention are a cation-responsive membrane selective for lithium in combination with sodium or potassium as the interfering cation in the form of a saturated solution of its salt, or a cation-responsive membrane selective for potassium in combination with calcium as the interfering cation in the form of a saturated solution of one of its salts, or a cation-responsive membrane selective for calcium in combination with sodium or potassium as the interfering cation in the form of a saturated solution of its salt. Although it is known that these are cross effects between ions, it has not previously been suggested that these effects could be exploited in a cation-sensitive electrode, or what combination of interfering cations could be used to advantage within this system which combines a hygroscopic binder material with a concentrated electrolyte fill.

It will be understood by those skilled in the art that the method of the present invention can be applied to almost all interfering cation/selective cation-responsive membrane combinations.

The cation-responsive membrane may be formed from (a) a polymeric material which has an inherent selectivity for the cation for which it is primarily selective, or (b) a polymeric material which has an ionophore, ligand or complexing agent incorporated into its structure to impart selective permeability. In the latter instance, the base polymeric material may be, for example, polyvinylchloride or polyurethane. It will be understood that for biomedical applications the cation-responsive membrane should be biocompatible. For lithium detection, the cation-responsive membrane may comprise a lithium selective polyvinylchloride membrane, for example a polyvinylchloride membrane which contains as the lithium ionophore N,N-dicyclohexyl-N,N-diisobutyl-cis-cyclohexane-1,2-dicarboxamide (ETH 1810 Fluka Chemicals). This lithium ionophore has a selectivity for lithium over sodium (logKPot/LiNa) of $-2.3$, i.e. it is about 200 times more responsive to lithium than to sodium and thus may be used in combination with an internal reference solution which contains a saturated solution of a sodium salt, for example sodium chloride. It also shows a selectivity for lithium over potassium similar to that for lithium over sodium and may thus be used in combination with an internal reference solution which contains a saturated solution of a potassium salt. An alternative membrane comprises high molecular weight PVC (33.1%) plasticized with bis (2-ethylhexyl) sebacate or bis (2-ethylhexyl)-adipate (66.2%) with 6,6-dibenzyl-14-crown-4 as the ionophore (0.66%) and an addition of potassium tetrakis (4-chlorophenyl) borate (0.044%) to improve the conductivity of the membrane and improve the selectivity of the membrane against anions.

For calcium detection, the cation-responsive membrane may comprise a calcium selective polyvinylchloride membrane, for example a polyvinyl chloride membrane which contains as the calcium ionophore diethyl-N,N'-[(4R, 5R) -4,5-dimethyl-1,8-dioxo-3,6-dioxaoctamethylene]-bis(12-methylamino-dodecanoate ETH 1001, Fluka Chemika). This calcium ionophore has a good selectivity for calcium over sodium or potassium and thus may be used in combination with an internal reference solution which contains a saturated solution of a sodium or potassium salt.

For potassium detection, the cation-responsive membrane may comprise a potassium selective polyvinylchloride membrane, for example a polyvinylchloride membrane which contains as the potassium ionophore valinomycin. This potassium ionophore has a good selectivity for potassium over calcium and thus may be used in combination with an internal reference solution which contains a saturated solution of a calcium salt.

The internal reference electrode may be, for example, a silver/silver chloride electrode. The silver/silver chloride electrode may be formed on the end of a conducting wire, which may be a silver wire or a stainless steel wire or other material coated with silver, the end portion of which is chloridized.

The internal reference solution contains a saturated solution of a salt of a cation other than the cation for which the cation-responsive membrane is primarily selective. The internal reference solution is formed in situ either by exposure to water in the atmosphere and/or during use. This is achieved by including a hygroscopic material which hydrates when the electrode is put into use to form the internal reference solution. Preferably the hygroscopic material is formed as a layer on the internal reference electrode in admixture with the salt of the cation for which the cation-responsive membrane is not primarily selective.

It will be understood that the internal reference solution must be compatible with the internal reference electrode. For example, when the internal reference electrode is a silver/silver chloride electrode, the internal reference solution will generally contain silver chloride and a soluble chloride salt of the interfering cation.

The hygroscopic material may be, for example, sorbitol. The inclusion of a hygroscopic material assists in rapid hydration thereby reducing the time for the cation-sensitive electrode to become activated when put into use. Indeed, the electrode following manufacture immediately starts to hydrate from water present in the atmosphere and is therefore never a fully dry system. The formation of a solidified layer on the internal reference electrode may be achieved, for example, by forming a melt of a relatively low melting point hygroscopic material, such as sorbitol, and then dissolving or dispersing the other ingredients required to form the internal reference solution into the melt. The internal reference electrode may then be dipped into this melt or the melt may be introduced into a tube, such as a polyvinyl-chloride tube, containing the internal reference electrode. The tube is then closed by the cation-responsive membrane being formed in situ over the end of the tube. The membrane may be formed, for example, by dipping the tube into a solution of the cation-responsive membrane in a suitable solvent, followed by drying.

The cation-selective electrode of the present invention may be used, for example, in biomedical applications, for example for monitoring the presence of a particular species in blood or other body fluids. For biomedical applications the component parts of the cation-selective electrodes must be biocompatible. A particular advantage of the device as described herein is that it may be minaturized and effective devices may be prepared which have outer diameters of less than 1 mm, for example 0.3 to 0.7 mm.

A particularly important application of the cation-selective electrode of the present invention is in a method of measuring cardiac output. Cardiac output is the volume of blood pumped by the heart per minute. A knowledge of the cardiac output can be very useful in the management of the critically ill patient. The current method of choice for measuring cardiac output is the thermodilution catheter. The dilution by the blood of a bolus of cold dextrose is used. There are two disadvantages to the method. Firstly, the catheter has to be passed through the heart and into the pulmonary artery. Secondly, the single use catheters are expensive (approximately £70 for the complete disposable parts). This method is widely used clinically at the present time.

An alternative method of measuring cardiac output is the dye dilution method. In principle this is the same as the thermodilution method, except that a dye is used instead of a drop in temperature. For a number of technical reasons it is not used clinically. It has however one possible advantage and that is that the sensor can be placed in any peripheral artery since the dye can thus pass the lungs.

We have found that the cardiac output in man and animals can be measured by measuring with a cation-selective electrode as hereinbefore described the dilution curves in the blood plasma flowing in a peripheral artery, of bolus injections into a central vein of a solution containing a cation, preferably lithium, which is not normally present in the plasma.

The present invention thus includes within its scope a method of measuring cardiac output in a human being which method comprises:

(i) injecting into a central vein of the human being a bolus injection of a solution of a cation which is not normally present in blood;

(ii) measuring the dilution of the cation in the blood plasma flowing in a peripheral artery using a cation-sensitive electrode which is sensitive to the cation injected in step (i); and (iii) calculating from the dilution data obtained in step (ii) the cardiac output.

Preferably the cation-sensitive electrode used in the method of the invention comprises an internal reference electrode, an internal reference solution and a cation-responsive membrane, the internal reference solution containing a saturated solution of a salt of a cation other than the cation for which the cation-responsive membrane is primarily selective, the internal reference solution being formed in situ by hydration of a combination of a hygroscopic material with the salt of the cation other than the cation for which the cation-responsive membrane is primarily selective, either by absorption of water from the atmosphere and/or by hydration of the hygroscopic material when the electrode is put into use thereby forming the internal reference solution.

By using a cation which is not normally present in the blood plasma, but for which a cation-selective electrode exists, dilution curves are obtained from a flow through cell containing the electrode, connected to a peripheral artery. The advantage of the method is that the injections of the salt containing the cation, made into a central vein, can be very small and yet provide satisfactory curves. The limit on the reduction of the quantity of the cation injected is determined by the selectivity of the cation-responsive membrane of the electrode for the cation over the other cations present in the plasma. Another limit is the degree to which the cation used is taken up by a single pass through the lungs. The cation must also be non-toxic in the doses used.

A specific example of the method of the present invention is the use of a cation-selective electrode which comprises a lithium selective cation-responsive membrane. A particular lithium selective cation-responsive membrane which may be used is a membrane which contains as the lithium ionophore N,N-dicyclo-hexyl-N-diisobutyl-cis-cyclohexane-1,2-dicarboxamide (ETH 1810, Fluka Chemika). As mentioned above, this ionophore provides a selectivity for lithium over sodium of $-2.3$ (log K Pot/LiNa), i.e. it is 200 times as sensitive to lithium as it is to sodium ions. The sodium ions normally present in the blood plasma generate a voltage at the electrode that corresponds to a low level of lithium. An alternative membrane comprises high molecular weight PVC (33.1%) plasticized with bis(2-ethylhexyl)sebacate or bis (2-ethylhexyl) adipate (66.2%) with 6,6-dibenzyl-14-crown-4 as the ionophore (0.66%) and an addition of potassium tetrakis (4-chlorophenyl)borate (0.044%) to improve the conductivity of the membrane and improve the selectivity of the membrane against anions. Satisfactory dilution curves can be obtained with concentration peaks of less than 0.5 mM Li. The lithium electrode, together with a reference electrode, may be housed in a flow through cell connected to a cannula inserted into a peripheral artery. Blood is allowed to flow through the cell when a measurement is required. The injection solution contains a lithium salt, preferably lithium chloride, although other lithium salts such as lithium carbonate may also be used.

BRIEF DESCRIPTION OF THE DRAWINGS

The present invention will be further described by way of example and with reference to the accompanying drawings in which.

DETAILED DESCRIPTION OF THE PREFERRED EMBODIMENTS

Figure 1:
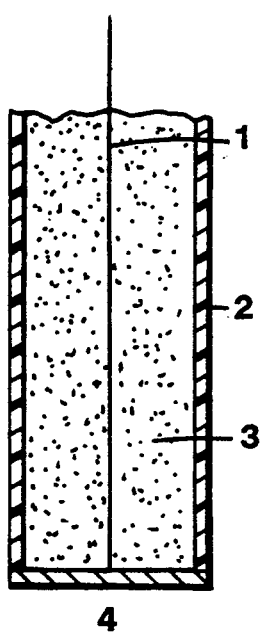
FIG. 1 illustrates, schematically, a cross-sectional view of the tip of a sensor in accordance with the present invention.

Referring to FIG. 1 of the drawings, a cation-sensitive electrode in accordance with the present invention comprises an internal reference electrode 1 centrally mounted in a polyvinylchloride (PVC), polytetrafluroethylene (PTFE) or polyurethane (PU) sleeve 2 having an outer diameter of about 0.8 mm. The internal reference electrode comprises a chloridized silver wire having an outer diameter of 0.125 mm. The internal reference electrode is coated with a layer 3 of a solid material which, in use of the electrode, is hydrated to form the internal reference solution. The tip of the PVC, PTFE or PU sleeve 2 is dipped into a solution of the cation-responsive membrane in tetrahydrofuran. In this particular example the cation-responsive membrane is polyvinylchloride which contains as a lithium ionophore N,N-dicyclohexyl-N,N-diisobutyl-cis-cyclo-hexane-1,2-dicarboxamide (ETH 1810, Fluka Chemika). An alternative membrane comprises high molecular weight PVC (33.1%) plasticized with bis(2-ethylhexyl)-sebacate or bis-(2-ethylhexyl)adipate (66.2%) with 6,6-dibenzyl-14-crown-4 as the ionophore (0.66%) and an addition of potassium tetrakis(4-chlorophenyl)borate (0.044%) to improve the conductivity of the membrane and improve the selectivity of the membrane against anions. Dipping of the PVC, PTFE or PU sleeve into the membrane solution, followed by drying, results in the formation of a cation-responsive membrane 4 across the tip of the tube. The membrane 4 is deposited onto the sleeve 2. The membrane generally has a thickness of 0.1 to 0.2 mm.

To form the layer 3 on electrode 1, the electrode is dipped into a melt of the following composition:

| Sorbitol | 10 grams |
| --- | --- |
| Sodium Chloride | 4 grams |
| Silver Chloride | 2% (approx) | and then withdrawn. On cooling, the melt solidifies to form the layer 3. Apart from the trace of silver chloride the fill is non-toxic. The electrolyte composition may also be introduced into a PVC, PTFE or PU sleeve containing the electrode 1 by suction before the membrane 4 is deposited onto the sleeve 2.

In the use of the cation-sensitive electrode in monitoring cardiac output, the electrode may be mounted through a 3-way tap with the spigot part removed so that the tip of the sensor emerges from the male luer fitting. The layer 3 on the electrode 1 is hydrated within a very short period of time once the cation-sensitive electrode contacts the blood as water ingresses through the membrane 4. The passage of water across the membrane 4 is accelerated by the presence of the sorbitol in layer 3. It will be understood that the amount of solid material 3 coated onto the electrode 1 is chosen, in combination with the knowledge of the volume of the sleeve 2, so that a saturated solution of sodium chloride will result on hydration of layer 3.

The cation-sensitive electrode is connected in a manner known per se to a reference electrode and to appropriate equipment to display and amplify the results obtained.

The lithium sensitive electrode described above had a potential compared to a saturated calomel electrode of approximately $-170$ mV in 0.15M molar NaCl.

A similar electrode may be prepared for the detection of calcium using as the ionophore in the polyvinylchloride membrane composition diethyl-N,N'[(4R,5R)]-4,5-dimethyl-1,8-dioxo-3,6-dioxaoctamethylene]-bis(12-methylamino-dodecanoate ETH 1001, Fluka Chemika). To form the layer 3 on electrode 1, the electrode is dipped into a melt of the same composition as for the lithium sensitive electrode.

The calcium sensitive electrode had a potential, compared to a saturated calomel electrode, of +6.5 mV for 1.0 mM $CaCl_2$ in 150 mM NaCl.

A similar electrode may also be prepared for the detection of potassium using as the ionophore in the polyvinylchloride membrane composition valinomycin. To form the layer 3 on electrode 1, the electrode is dipped into a melt comprising

| | |
|---|---|
| Sorbitol | 10 grams |
| Calcium Chloride | 4 grams |
| Silver Chloride | 2% (approx) | and then withdrawn. On cooling, the melt solidifies to form the layer 3.

The potassium sensitive electrode had a potential, compared to a saturated calomel electrode, of −110 mV for 8 mM KCl in 142 mM NaCl.

Figure 2:
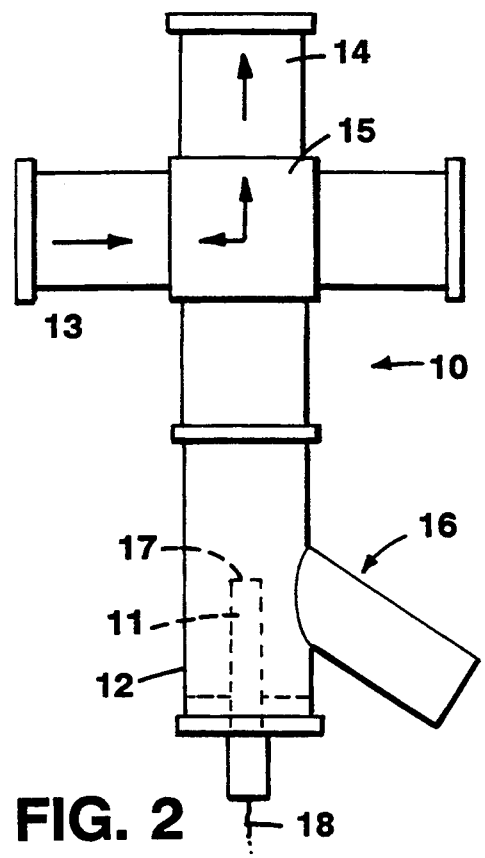
FIG. 2 illustrates schematically, a sensor in accordance with the present invention incorporated into a sensor assembly and tap ready to be used in a patient.

Referring to FIG. 2 of the drawings, a combination of a tap and Y-can 10 has a lithium sensor 11 in accordance with the invention inserted into an arm 12 thereof. The tap has one arm 13 connected to the arterial line and one arm 14 connected to a blood pressure monitoring system, the arrows showing the direction of blood flow. When the sensor is not in use the arterial line is connected to the blood pressure monitoring system by tap 15.

If a determination of cardiac output is required then tap 15 is turned 90° anti-clockwise thus connecting the arterial line to the Y-can 16, which functions as a flow-through cell. The patient is injected with a small amount of lithium through a central venous catheter and blood is allowed to flow through the Y-can across the face 17 of the sensor 11. The sensor is connected via 18 to an appropriate electrical connector and appropriate electronic measuring apparatus. Approximately 4 to 10 mls of blood are withdrawn over 20 seconds. As lithium passes from the venous to the arterial lines the sensor detects the changing concentrations and from this information the cardiac output is calculated.

The tap is then turned 90° anti-clockwise and any remaining blood flushed from the Y-can.

The tap is then returned to its starting position leaving the arterial line connected to the blood pressure monitor and the sensor ready for the next procedure.

The use of the lithium sensitive electrode of a preferred embodiment of the present invention for monitoring cardiac output in man is described with reference to the following Example.

EXAMPLE

Patients

Nine patients were studied during the immediate postoperative period following either coronary artery bypass grafting (7 patients) or aortic valve replacement (2 patients). The patients' ages and weights ranged from 38–73 years and 64–90 kg and none of them was receiving oral lithium.

After induction of anaesthesia a Swan-Ganz catheter (Fast Flow R.E.F. catheter, Baxter) was inserted via the right internal jugular vein. The catheter was advanced until the pressure recorded from the injectate port showed this to be in the right ventricle. The catheter was then withdrawn 2 cm further than the point at which the pressure changed from ventricular to atrial. An arterial cannula (22, 20 or 18 gauge, depending on the normal practice of the anaesthetist) was inserted into a radial or brachial artery. During the study, which took less than an hour, the patients were sedated with morphine and propofol (Diprivan) infusions and ventilated with a Servo ventilator.

Thermodilution Cardiac Output

These measurements were carried out using a COM 11 Baxter Thermodilution computer. Injections of 10 ml ice cold 5% dextrose were made into the right atrium to obtain triplicate readings. The curve obtained following the first injection was always rejected and only rarely were more than 3 further injections needed. No attempt was made to synchronize injection with the phase of the respiratory cycle.

Lithium Dilution Cardiac Output

The lithium sensor, illustrated in FIG. 1 consisted of a 2–3 cm length of 18 gauge PTFE tubing which contained an internal reference electrode and had a PVC membrane dip-cast over one end. The membrane contained the crown ether lithium ionophore 6,6-Dibenzyl-14-crown-4 which made it selectively permeable to $Li^+$. The sensor was mounted in a Y-connector (Vygon, 889). The voltage across the membrane was recorded between 2 chloridized silver wires, one in the internal 'fill' and the other in the lumen of the Y-connector. This second wire was coated with polyurethane (Tecoflex) to protect the silver chloride from plasma proteins. The voltage was recorded via an optically isolated preamplifier displayed on a chart recorder and recorded on magnetic tape for later analysis.

Before mounting the sensors in the Y-connectors they were tested in vitro to ensure that the voltages recorded in saline and 1 mM $[Li^+]$ in saline were correct. For these sensors a change from 0.15M NaCl to 1 mM LiCl in 0.15M NaCl $[Li^+]$ should produce a 10 mV change in membrane potential. The sensors were then sealed into one limb of the Y-connectors and sterilized by immersion in glutaraldehyde. The glutaraldehyde was washed out with saline and the calibration checked again. To use the sensor the Y-connector with a 3-way tap was connected to a second 3-way tap which was attached to the hub of the arterial cannula. A 10 cm length of tubing and 20 ml syringe were connected to the open limb of the Y-connector so that blood could flow past the sensor into the syringe. The flow varied depending on the size of the arterial cannula and blood pressure, but was in the range of from 15–30 ml $min^{-1}$. At no stage did blood or flushing fluid pass back over the sensor into the arterial catheter. Blood was allowed to flow past the sensor and when a stable baseline voltage was being recorded, 0.6 mmol LiCl (2 ml of a 0.3M solution) was injected into the superior vena cava via one of the catheters in the right internal jugular vein. The deadspace of this catheter had previously been cleared with the LiCl solution and care was taken to inject exactly 2 ml. When the second lithium curve had been obtained another sensor was attached and the same procedure repeated. Each lithium sensor was used to make 2 cardiac output measurements. Between these 2 measurements 3 thermal dilution measurements were made. The lithium and thermal dilution estimates were therefore not simultaneous but the intervals between them were as short as possible, usually less than 1 minute. The mean of the lithium values was compared with the mean of the 3 thermal dilution values to give one lithium/thermal dilution comparison. Up to 3 sensors were tested in this way on each patient and results were obtained from 22 electrodes in the 9 patients.

The sensor gives a constant reading in blood in the absence of any $Li^+$ due to the cross-sensitivity of the ligand with $Na^+$, so that it reads the background plasma $[Na^+]$ level (140 mM) as approximately 2.4 mM $[Li^+]$. The injections of LiCl (0.6 mmol) produce small increments on top of this background voltage and over this narrow range the voltage change of the sensor approximates closely to a linear response to the $[Li^+]$. The linearity of the response over this range was confirmed by adding aliquots of $Ll^+$ to blood in vitro.

Figure 3:
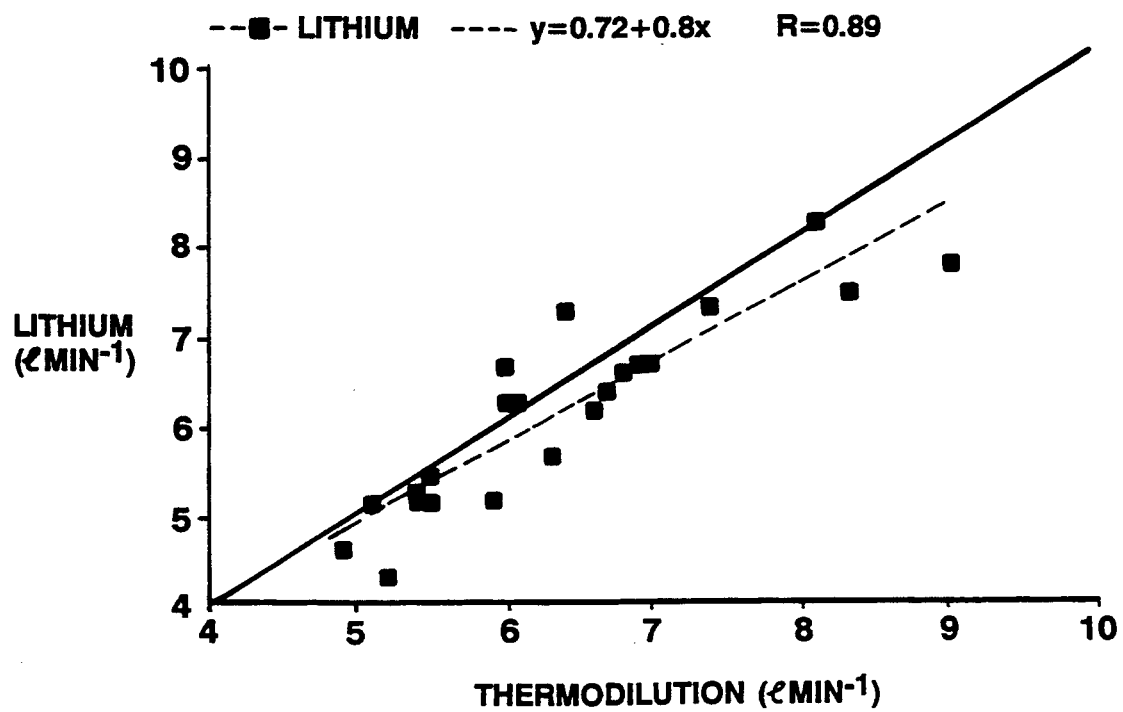
FIG. 3 shows the correlation between lithium measurements and thermal dilution measurements for cardiac output measurement in an in-vivo test.

The correlation between the lithium and thermal dilution measurements is shown in FIG. 3. The average of all the lithium readings was 6.1 liter $min^{-1}$ and of the dilution readings was 6.4 liter $min^{-1}$, the thermal dilution estimate was therefore on average 300 ml $min^{-1}$ higher than the lithium readings.

We claim:

1. A cation-sensitive electrode which comprises an internal reference electrode, an internal reference solution and a cation-responsive membrane, characterized in that the internal reference solution contains a saturated solution of a salt of a cation other than the cation for which the cation-responsive membrane is primarily selective, the internal reference solution is formed in situ by hydration of a combination of a hygroscopic material with the salt of the cation other than the cation for which the cation-responsive membrane is primarily selective, either by absorption of water from the atmosphere and/or by hydration of the hygroscopic material when the electrode is put into use, thereby forming the internal reference solution.

2. A cation-sensitive electrode as claimed in claim 1 wherein the cation-responsive membrane is formed from a polymeric material which has an inherent selectivity for the cation for which the membrane is primarily selective.

3. A cation-sensitive electrode as claimed in claim 1 wherein the cation-responsive membrane is formed from a polymeric material which has an ionophore, ligand or complexing agent incorporated into the membrane structure to impart selective permeability.

4. A cation-sensitive electrode as claimed in claim 3 wherein the cation-responsive membrane comprises a lithium selective polyvinylchloride membrane and the internal reference solution comprises a saturated solution of a sodium or potassium salt.

5. A cation-sensitive electrode as claimed in claim 4 wherein the lithium selective polyvinylchloride membrane contains as the lithium ionophore N,N-dicyclohexyl-N,N-diisobutyl-cis-cyclo-hexane-1,2-dicarboxamide or 6,6-dibenzyl-14-crown-4.

6. A cation-sensitive electrode as claimed in claim 3 wherein the cation-responsive membrane comprises a calcium selective polyvinylchloride membrane and the internal reference solution comprises a saturated solution of a sodium or potassium salt.

7. A cation-sensitive electrode as claimed in claim 6 wherein the calcium selective polyvinylchloride membrane contains as the calcium ionophore diethyl-N,N'-bis(12-methylamino-dodecanoate).

8. A cation-sensitive electrode as claimed in claim 3 wherein the cation-responsive membrane comprises a potassium selective polyvinylchloride membrane and the internal reference solution comprises a saturated solution of a calcium salt.

9. A cation-sensitive electrode as claimed in claim 8 wherein the potassium selective polyvinylchloride membrane contains as the potassium ionophore valinomycin.

10. A cation-sensitive electrode as claimed in claim 1 wherein the hygroscopic material is formed as a layer on the internal reference electrode in admixture with the salt of the cation for which the cation-responsive membrane is not primarily selective.

11. A cation-selective electrode as claimed in claim 1 wherein the hygroscopic material is sorbitol.

12. A method of measuring cardiac output in a human being which method is characterized in that it comprises:
    (i) injecting into a central vein of the human being a bolus injection of a solution of a cation which is not normally present in blood;
    (ii) measuring the dilution of the cation in the blood plasma flowing in a peripheral artery using a cation-sensitive electrode which is sensitive to the cation injected in step (i); and
    (iii) calculating from the dilution data obtained in step (ii) the cardiac output.

13. A method as claimed in claim 12 wherein the cation-sensitive electrode comprises an internal reference electrode, an internal reference solution and a cation-responsive membrane, the internal reference solution containing a saturated solution of a salt of a cation other than the cation for which the cation-responsive membrane is primarily selective, the internal reference solution is formed in situ by hydration of a combination of a hygroscopic material with the salt of the cation other than the cation for which the cation-responsive membrane is primarily selective, either by absorption of water from the atmosphere and/or by hydration of the hygroscopic material when the electrode is put into use thereby forming the internal reference solution.

14. A method as claimed in claim 13 wherein the cation-responsive membrane of the cation-sensitive electrode is formed from a polymeric material which has an ionophore, ligand or complexing agent incorporated into the membrane structure to impart selective permeability.

15. A method as claimed in claim 14 wherein the cation-responsive membrane comprises a lithium selective polyvinylchloride membrane and the internal reference solution comprises a saturated solution of a sodium or potassium salt.

16. A method as claimed in claim 14 or claim 15 wherein the lithium selective polyvinylchloride membrane contains as the lithium ionophore N,N-dicyclohexyl-N,N-diisobutyl-cis-cyclo-hexane-1,2-dicarboxamide or 6,6-dibenzyl-14-crown-4.

17. A method as claimed in claim 13 wherein the hygroscopic material is formed as a layer on the internal reference electrode in admixture with the salt of the cation for which the cation-responsive membrane is not primarily selective.

18. A method as claimed in claim 13 wherein the hygroscopic material is sorbitol.

19. A method as claimed in claim 12 or claim 13 wherein the injection comprises a lithium solution.

20. A method as claimed in claim 19 wherein the lithium solution comprises lithium chloride or lithium carbonate.

* * * * *

UNITED STATES PATENT AND TRADEMARK OFFICE
CERTIFICATE OF CORRECTION

PATENT NO.   : 5,395,505

DATED        : March 7, 1995

INVENTOR(S)  : David M. Band and Robert A.F. Linton

It is certified that error appears in the above-identified patent and that said Letters Patent is hereby corrected as shown below:

Col. 4, line 29, "ξ70" should be --£70--.

Col. 9, claim 7, line 61, after "N,N'-" insert
--[(4R,5R)-4,5-dimethyl-1,8-dioxo-3,6-dioxaoctamethylene]- --.

Signed and Sealed this

Thirtieth Day of April, 1996

Attest:

BRUCE LEHMAN

Attesting Officer

Commissioner of Patents and Trademarks